United States Patent
Azuma

(10) Patent No.: US 10,730,819 B2
(45) Date of Patent: Aug. 4, 2020

(54) NAPHTHALENEDICARBOXYLIC ACID DICHLORIDE PRODUCTION METHOD

(71) Applicant: KYOCERA Document Solutions Inc., Osaka (JP)

(72) Inventor: Jun Azuma, Osaka (JP)

(73) Assignee: KYOCERA Document Solutions Inc., Osaka (JP)

( * ) Notice: Subject to any disclaimer, the term of this patent is extended or adjusted under 35 U.S.C. 154(b) by 0 days.

(21) Appl. No.: 16/575,125

(22) Filed: Sep. 18, 2019

(65) Prior Publication Data

US 2020/0115313 A1    Apr. 16, 2020

(30) Foreign Application Priority Data

Oct. 11, 2018    (JP) .................................. 2018-192612

(51) Int. Cl.
*C07C 51/60* (2006.01)
*B01J 31/02* (2006.01)

(52) U.S. Cl.
CPC ........... *C07C 51/60* (2013.01); *B01J 31/0247* (2013.01); *B01J 2231/40* (2013.01); *B01J 2531/002* (2013.01)

(58) Field of Classification Search
CPC ... C07C 51/60; B01J 31/0247; B01J 2231/40; B01J 2531/002
USPC ........................................................ 562/861
See application file for complete search history.

(56) References Cited

FOREIGN PATENT DOCUMENTS

JP    2009298753 A    12/2009
JP    2012136502 A    7/2012

*Primary Examiner* — Deborah D Carr
(74) *Attorney, Agent, or Firm* — Studebaker & Brackett PC

(57) ABSTRACT

A naphthalenedicarboxylic acid dichloride production method includes causing a reaction between naphthalenedicarboxylic acid and a chlorinating agent at a reaction temperature of 20° C. or higher and 75° C. or lower in presence of a solvent including tetrahydrofuran. The causing a reaction in the naphthalenedicarboxylic acid dichloride production method is preferably performed in presence of N,N-disubstituted formamide.

5 Claims, No Drawings

NAPHTHALENEDICARBOXYLIC ACID DICHLORIDE PRODUCTION METHOD

INCORPORATION BY REFERENCE

The present application claims priority under 35 U.S.C. § 119 to Japanese Patent Application No. 2018-192612, filed on Oct. 11, 2018. The contents of this application are incorporated herein by reference in their entirety.

BACKGROUND

The present disclosure relates to a naphthalenedicarboxylic acid dichloride production method.

Naphthalenedicarboxylic acid dichloride is useful as a resin raw material or a reaction intermediate of various compounds. A known naphthalenedicarboxylic acid dichloride production method is a method for example by which 2,6-naphthalenedicarboxylic acid dichloride is produced in a manner that 2,6-naphthalenedicarboxylic acid, thionyl chloride, and N,N-dimethylformamide are caused to react together. Another production method is also proposed by which 2,6-naphthalenedicarboxylic acid dichloride is produced in a manner that 2,6-naphthalenedicarboxylic acid and an imidoyl chloride compound are caused to react together in a large amount of a solvent (for example, 1,4-dioxane or 1,2-dimethoxyethane). A still another method is proposed, as a production method of furandicarboxylic acid dichloride that is similar to naphthalenedicarboxylic acid dichloride, by which 2,5-furandicarboxylic acid dichloride is produced in a manner that 2,5-furandicarboxylic acid and a chlorinating agent are caused to react together at a specific reaction temperature for a specific reaction time in presence of N,N-disubstituted formamide.

SUMMARY

A naphthalenedicarboxylic acid dichloride production method according to an aspect of the present disclosure includes causing a reaction between naphthalenedicarboxylic acid and a chlorinating agent at a reaction temperature of 20° C. or higher and 75° C. or lower in presence of a solvent including tetrahydrofuran.

DETAILED DESCRIPTION

The following describes an embodiment of the present disclosure in detail. However, the present disclosure is by no means limited to the following embodiment. The present disclosure can be practiced within a scope of objects of the present disclosure with alterations made as appropriate. Although some overlapping explanations may be omitted as appropriate, such omission does not limit the gist of the present disclosure. Unless otherwise stated, one of the following components may be used independently or two or more of the following compounds may be used in combination.

<Naphthalenedicarboxylic Acid Dichloride Production Method>

A naphthalenedicarboxylic acid dichloride production method according to an embodiment of the present disclosure includes causing a reaction between naphthalenedicarboxylic acid and a chlorinating agent at a reaction temperature of 20° C. or higher and 75° C. or lower in a solvent including tetrahydrofuran (also referred to below as a reaction step). In the naphthalenedicarboxylic acid dichloride production method according to the present embodiment, the reaction step is preferably performed in presence of N,N-disubstituted formamide.

Naphthalenedicarboxylic acid dichloride is useful as a resin raw material or a reaction intermediate of various compounds. Examples of a resin of which a raw material is naphthalenedicarboxylic acid dichloride include polyarylate resins. Polyarylate resins can each be used for example as a binder resin in a photosensitive layer of an electrophotographic photosensitive member.

By the naphthalenedicarboxylic acid dichloride production method according to the present embodiment, high-purity naphthalenedicarboxylic acid dichloride can be produced with high productivity. Specifically, by the naphthalenedicarboxylic acid dichloride production method according to the present embodiment, naphthalenedicarboxylic acid dichloride for example having a purity of 99% by mass or higher can be produced with a high percentage yield (for example, 80% or higher) while adhesion of produced naphthalenedicarboxylic acid dichloride to a wall surface of a reaction vessel can be inhibited. Presumably, the reason therefor is as follows.

In naphthalenedicarboxylic acid dichloride production methods, both a row material compound (naphthalenedicarboxylic acid) and a product (naphthalenedicarboxylic acid dichloride) tend to have low solubility in a typical solvent. Therefore, a phenomenon in which the raw material compound insufficiently dissolves in a reaction solution or a phenomenon in which the product are crystalized to cover the raw material compound occurs by known production methods to reduce a purity and a percentage yield of the product. Furthermore, in the known production methods, the product tends to adhere to the wall surface of the reaction vessel and the percentage yield and the productivity accordingly tend to further reduce. The above situation can be improved to some extent by a method in which an amount of the solvent is increased to reduce each concentration of the raw material compound and the product in the reaction solvent. However, the above method increases production cost due to necessity of a larger amount of the solvent and reduces mass yield per capacity of the reaction vessel. Therefore, sufficient improvement in productivity cannot be achieved. By contrast, the production method according to the present embodiment uses a solvent including tetrahydrofuran to increase each solubility of the raw material compound and the product in the reaction solution. Furthermore, the reaction temperature in the production method according to the present embodiment is 20° C. or higher and 75° C. or lower, thereby inhibiting an undesirable reaction that may be caused in high temperature (for example, a reaction accompanying coloring). Therefore, by the production method according to the present embodiment, high-purity naphthalenedicarboxylic acid dichloride can be produced and adhesion of the product to the wall surface of the reaction vessel can be inhibited. Thus, high productivity (particularly, mass productivity) can be achieved.

In the reaction step, naphthalenedicarboxylic acid is chlorinated through a reaction represented by the following chemical equation (R). In the following chemical equation (R), a compound represented by general formula (a) is naphthalenedicarboxylic acid and a compound represented by general formula (A) is naphthalenedicarboxylic acid dichloride.

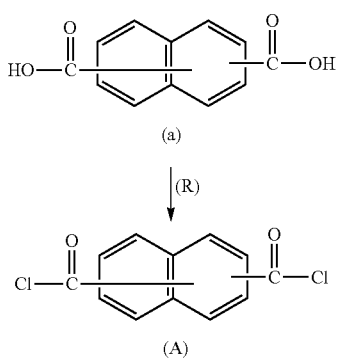

(a)

↓(R)

(A)

Examples of a combination of the raw material compound and the product in the reaction step include:

(1) 1,2-naphthalenedicarboxylic acid and 1,2-naphthalenedicarboxylic acid dichloride;
(2) 1,3-naphthalenedicarboxylic acid and 1,3-naphthalenedicarboxylic acid dichloride;
(3) 1,4-naphthalenedicarboxylic acid and 1,4-naphthalenedicarboxylic acid dichloride;
(4) 1,5-naphthalenedicarboxylic acid and 1,5-naphthalenedicarboxylic acid dichloride;
(5) 1,6-naphthalenedicarboxylic acid and 1,6-naphthalenedicarboxylic acid dichloride;
(6) 1,7-naphthalenedicarboxylic acid and 1,7-naphthalenedicarboxylic acid dichloride;
(7) 1,8-naphthalenedicarboxylic acid and 1,8-naphthalenedicarboxylic acid dichloride;
(8) 2,3-naphthalenedicarboxylic acid and 2,3-naphthalenedicarboxylic acid dichloride;
(9) 2,6-naphthalenedicarboxylic acid and 2,6-naphthalenedicarboxylic acid dichloride; and
(10) 2,7-naphthalenedicarboxylic acid and 2,7-naphthalenedicarboxylic acid dichloride.

The above combination (3) and (9) are each preferable as the combination of the raw material compound and the product in the reaction step. That is, it is preferable that the naphthalenedicarboxylic acid is 1,4-naphthalenedicarboxylic acid and the naphthalenedicarboxylic acid dichloride is 1,4-naphthalenedicarboxylic acid dichloride or that the naphthalenedicarboxylic acid is 2,6-naphthalenedicarboxylic acid and the naphthalenedicarboxylic acid dichloride is 2,6-naphthalenedicarboxylic acid dichloride. When either of the above combinations is employed, 2,6-naphthalenedicarboxylic acid dichloride or 1,4-naphthalenedicarboxylic acid dichloride can be obtained that is particularly useful as a resin raw material and an intermediate of various compounds.

Naphthalenedicarboxylic acid is preferably added in the reaction step in an amount of at least 10% by mass and no greater than 30% by mass relative to a total amount of the reaction solution, and more preferably at least 15% by mass and no greater than 25% by mass. As a result of the amount of naphthalenedicarboxylic acid being at least 10% by mass, mass yield of the product relative to a capacity of the reaction vessel can be increased. As a result of the amount of naphthalenedicarboxylic acid being no greater than 30% by mass, the raw material compound and the product can further readily dissolve in the reaction solution, and high-purity naphthalenedicarboxylic acid dichloride can accordingly be produced with high productivity.

Tetrahydrofuran serves as a main solvent of the reaction solution in the reaction step. As a result of tetrahydrofuran being used as a main solvent, each solubility of the raw material compound and the product in the reaction solution can be increased. Tetrahydrofuran is included in the solvent of the reaction solution preferably in an amount of at least 80% by mass, more preferably in an amount of at least 95% by mass, and particularly preferably in an amount of 100% by mass. Here, the solvent in the production method according to the present embodiment is a component among liquid components included in the reaction solution other than the chlorinating agent and N,N-disubstituted formamide.

Tetrahydrofuran is added in the reaction step preferably in an amount of at least 35% by mass and no greater than 70% by mass relative to the total amount of the reaction solution, and more preferably in an amount of at least 40% by mass and no greater than 60% by mass. As a result of the amount of tetrahydrofuran being at least 35% by mass, the raw material compound and the product can further readily dissolve in the reaction solution. Thus, higher-purity naphthalenedicarboxylic acid dichloride can be produced with higher productivity. As a result of the amount of tetrahydrofuran being no greater than 70% by mass, cost of the solvent can be reduced and mass yield of the product relative to the capacity of the reaction vessel can be increased.

Examples of the chlorinating agent include thionyl chloride, oxalyl chloride, phosgene, phosphoryl chloride, sulfuryl chloride, phosphorus trichloride, phosphorus pentachloride, and phosphorus oxychloride. Among the above examples, thionyl chloride and oxalyl chloride are preferable and thionyl chloride is further preferable.

The chlorinating agent is preferably added in the reaction step in an amount of at least 1.5 moles and no greater than 6.0 moles relative to 1 mole of naphthalenedicarboxylic acid, and more preferably in an amount of at least 2.5 moles and no greater than 3.5 moles. As a result of the chlorinating agent being added in an amount of at least 1.5 moles and no greater than 6.0 moles relative to 1 mole of naphthalenedicarboxylic acid, high-purity naphthalenedicarboxylic acid dichloride can be produced with high productivity.

The reaction step is preferably performed in presence of N,N-disubstituted formamide. As a result of performing the reaction step in the presence of N,N-disubstituted formamide, production of naphthalenedicarboxylic acid dichloride is promoted.

An example of N,N-disubstituted formamide is a compound represented by the following general formula (1).

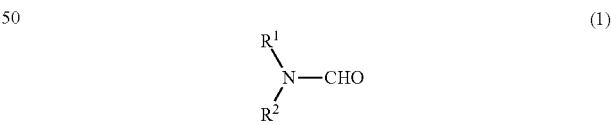

In general formula (1), $R^1$ and $R^2$ each represent, independently of one another, an alkyl group having a carbon number of at least 1 and no greater than 10.

An alkyl group having a carbon number of at least 1 and no greater than 10 is an unsubstituted straight chain or branched chain alkyl group. Examples of an alkyl group having a carbon number of at least 1 and no greater than 10 include a methyl group, an ethyl group, an n-propyl group, an isopropyl group, an n-butyl group, a sec-butyl group, a tert-butyl group, an n-pentyl group, an isopentyl group, a neopentyl group, a 1,2-dimethylpropyl group, a straight chain or branched chain hexyl group, a straight chain or branched chain heptyl group, a straight chain or branched chain octyl group, and a straight chain or branched chain decyl group.

An alkyl group that may be represented by $R_1$ or $R_2$ is preferably an alkyl group having a carbon number of at least 1 and no greater than 4, and more preferably a methyl group or an ethyl group. Preferably, $R_1$ and $R_2$ are the same as each other.

Examples of N,N-disubstituted formamide include N,N-dimethylformamide and N,N-diethylformamide.

N,N-disubstituted formamide is preferably added in the reaction step in an amount of at least 0.05% by mass and no greater than 0.50% by mass relative to the total amount of the reaction solution, and more preferably at least 0.10% by mass and no greater than 0.30% by mass. As a result of N,N-disubstituted formamide being added in an amount of at least 0.05% by mass and no greater than 0.50% by mass relative to the total amount of the reaction solution, higher-purity naphthalenedicarboxylic acid dichloride can be produced with higher productivity.

Although it is preferable to use only naphthalenedicarboxylic acid, the chlorinating agent, tetrahydrofuran, and N,N-disubstituted formamide in the reaction step, another component may be further added.

A reaction temperature in the reaction step is preferably 50° C. or higher and 75° C. or lower, and more preferably 70° C. or higher and 75° C. or lower. The reaction step is preferably performed under reflux. The reaction time in the reaction step is preferably 30 minutes or longer and 48 hours or shorter, more preferably 1 hour or longer and 12 hours or shorter, and further preferably 3 hours or longer and 5 hours or shorter. The reaction step is preferably performed under stirring.

The production method according to the present embodiment may further include, after the reaction step, adding an organic solvent to the reaction solution. When the production method according to the present embodiment further includes the adding an organic solvent as above, higher-purity naphthalenedicarboxylic acid dichloride can be produced with higher productivity. Examples of the organic solvent include alkylbenzenes such as toluene and xylene. Among alkylbenzenes, xylene is preferable. The organic solvent is added preferably in an amount of at least 10 parts by mass and no greater than 150 parts by mass relative to 100 parts by mass of the reaction solution, and more preferably in an amount of at least 20 parts by mass and no greater than 80 parts by mass.

Naphthalenedicarboxylic acid dichloride generated in the reaction step precipitates as crystals after the reaction step (where the adding an organic solvent is performed, after the adding an organic solvent). In order to promote precipitation of naphthalenedicarboxylic acid dichloride, cooling may be performed as necessary after the reaction step (where the adding an organic solvent is performed, after the adding an organic solvent). No particular limitations are placed on a cooling temperature other than being lower than the reaction temperature, and the cooling temperature may be for example 10° C. or higher and 25° C. or lower.

Crystallized naphthalenedicarboxylic acid dichloride can be collected by removing unnecessary components (for example, the solvent and remaining chlorinated matter) through purification of the reaction solution. Examples of a purification method include one or a combination of two or more of filtration, washing, crystallization, pressure reduction (for example, vacuum drying), and chromatography.

EXAMPLES

The following provides more specific description of the present disclosure through use of Examples. The present disclosure is not limited to the scope of the Examples. Note that a percentage yield of naphthalenedicarboxylic acid dichloride represents a ratio of a mass yield of the product (mass yield including mass yield of impurities) to a theoretical mass yield.

Naphthalenedicarboxylic acid dichloride is unstable, and therefore, high-performance liquid chromatography (HPLC) determination by the following method was performed to measure a purity of naphthalenedicarboxylic acid dichloride. First, naphthalenedicarboxylic acid dichloride was caused to react with diethylamine to be changed into carboxydiamide body. The HPLC determination was performed on the resultant carobxydiaminde body, and an amount of naphthalenedicarboxylic acid dichloride was calculated based on the result of measurement.

The reaction between naphthalenedicarboxylic acid dichloride and diethylamine was performed by the following method. First, 0.010 g of a sample (specifically, a sample including naphthalenedicarboxylic acid dichloride) and 5.0 g of acetonitrile were added into a 70-mL mayonnaise bottle, and the sample was dissolved in acetonitrile by hand-shaking. To the resultant mixed liquid, 0.080 g of diethylamine was added, and then, the resultant mixed liquid was hand-shaken. After the hand-shaking, 4.0 g of water was further added and the resultant mixed liquid was hand-shaken again. Thereafter, the resultant mixed liquid was left for stand for 5 minutes or longer. The mixed liquid left for stand was used as an HPLC analysis sample.

(HPLC)

Conditions for HPLC in the present examples are listed below.

Measuring device: "ELITE LaChrom", product of Hitachi, Ltd.

Detection wavelength: 225 nm

Column: "INERTSIL (registered Japanese trademark) ODS-3", product of GL Sciences Inc. (inner diameter: 4.6 mm, length: 25 cm)

Column temperature: 40° C.

Developing solvent: mobile phase A acetonitrile, mobile phase B 0.1% phosphoric acid aqueous solution Flow rate: 1 mL/minute Sample injection amount: 1 µL (Naphthalenedicarboxylic Acid)

As a raw material compound for producing naphthalenedicarboxylic acid dichloride, each of 2,6-naphthalenedicarboxylic acid represented by the following chemical formula (n-1) and 1,4-naphthalenedicarboxylic acid represented by the following chemical formula (n-2) was prepared.

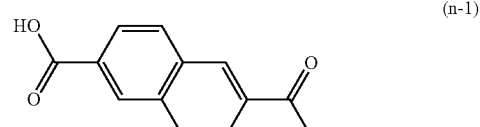

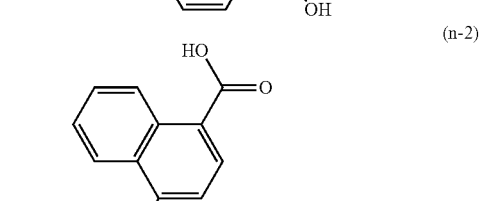

Example 1

A 500-mL three-necked flask equipped with an Allihn condenser and a thermometer was charged with a stir bar and 25.0 g (115.6 mmol) of 2,6-naphthalenedicarboxylic acid as a raw material compound, and deaeration and nitrogen substitution were performed thereon. Thereafter, 71.25 g of a tetrahydrofuran solution containing thionyl chloride (a mixed liquid of 41.25 g (347.6 mmol) of thionyl chloride and 30.0 g of tetrahydrofuran, concentration of thionyl chloride: 57.9% by mass), 37.0 g of tetrahydrofuran, and 4 drops (approximately 0.19 g) of N,N-dimethylformamide as a catalyst were sequentially added into the three-necked flask, and the resultant mixture was stirred using a magnetic stirrer to cause a reaction under reflux for 4 hours. During the reaction, the reaction solution was suspended at a temperature of 73° C. The reaction solution after the reaction was allowed to cool at room temperature (23° C.), thereby precipitating a large amount of crystals. The crystals precipitated in the reaction solution was then filtered out using a filtration device, and the crystals filtered by the filtration device were washed by being showered with cyclohexane. The washed crystals were vacuum dried at 70° C. for 12 hours to yield 25.5 g of a product including 2,6-naphthalenedicarboxylic acid dichloride (percentage yield 87.1%, purity measured by HPLC 99.70% by mass).

Example 2

A 500-mL three-necked flask equipped with an Allihn condenser and a thermometer was charged with a stir bar and 25.0 g (115.6 mmol) of 2,6-naphthalenedicarboxylic acid as a raw material compound, and deaeration and nitrogen substitution were performed thereon. Thereafter, 71.25 g of a tetrahydrofuran solution containing thionyl chloride (a mixed liquid of 41.25 g (347.6 mmol) of thionyl chloride and 30.0 g of tetrahydrofuran, concentration of thionyl chloride: 57.9% by mass), 37.0 g of tetrahydrofuran, and 4 drops (approximately 0.19 g) of N,N-dimethylformamide as a catalyst were sequentially added into the three-necked flask, and the resultant mixture was stirred using a magnetic stirrer to cause a reaction under reflux for 4 hours. During the reaction, the reaction solution was suspended at a temperature of 73° C. After the reaction, 50 g of xylene was added to the reaction solution and stirring was performed thereon for 10 minutes under reflux. After the stirring, the reaction solution was allowed to cool at room temperature (23° C.), thereby precipitating a large amount of crystals. Subsequently, pressure reduction (60° C., 0.040 MPa, for 60 minutes) was performed on the reaction solution to remove thionyl chloride and tetrahydrofuran. After the pressure reduction, the reaction solution was filtered out using a filtration device to remove remaining liquid components (mainly, xylene). The crystals filtered on the filtration device was showered with cyclohexane to be washed. The washed crystals were vacuum dried at 70° C. for 12 hours to yield 26.4 g of a product including 2,6-naphthalenedicarboxylic acid dichloride (percentage yield 90.3%, purity measured by HPLC 99.42% by mass).

Naphthalenedicarboxylic acid dichloride of each of Examples 3 to 8 were produced according to the same method as that of Example 1 in all aspects other than the following changes.

Example 3

While 2,6-naphthalenedicarboxylic acid was used as a raw material compound in Example 1, 25.0 g (115.6 mmol) of 1,4-naphthalenedicarboxylic acid was used as a raw material compound in Example 3.

Examples 4 and 5

While the reaction time was 4 hours in Example 1, the reaction times in Examples 4 and 5 were 6 hours and 2 hours, respectively.

Example 6

While the reaction was caused under reflux (73° C.) for 4 hours in Example 1, the reaction was caused for 24 hours at a temperature of 30° C. (under non-reflux) in Example 6.

Example 7

The tetrahydrofuran solution containing thionyl chloride, tetrahydrofuran, and N,N-dimethylformamide were sequentially added into the three-necked flask charged with the raw material compound in Example 1. By contrast, in Example 7, 74.12 g of a tetrahydrofuran solution containing oxalyl chloride (a mixed liquid of 44.12 g (347.6 mmol) of oxalyl chloride and 30 g of tetrahydrofuran, concentration of oxalyl chloride: 59.5% by mass), 37.0 g of tetrahydrofuran, and 4 drops (approximately 0.19 g) of N,N-dimethylformamide as a catalyst were sequentially added into the three-necked flask charged with the raw material compound.

Example 8

While N,N-dimethylformamide was used as a catalyst in Example 1, 4 drops (approximately 0.18 g) of N,N-diethylformamide was used as a catalyst in Example 8.

Comparative Example 1

A 500-mL three-necked flask (reaction vessel) equipped with an Allihn condenser and a thermometer was charged with a stir bar and 25.0 g (115.6 mmol) of 2,6-naphthalenedicarboxylic acid as a raw material compound, and deaeration and nitrogen substitution were performed thereon. Thereafter, 100 g of thionyl chloride and N,N-dimethylformamide (4 drops, approximately 0.19 g) as a catalyst were sequentially added into the three-necked flask, and the resultant mixture was stirred using a magnetic stirrer to cause a reaction under reflux for 4 hours. During the reaction, the reaction solution was suspended at a temperature of 74° C. After the reaction, the reaction solution was allowed to cool at room temperature (23° C.), thereby precipitating a large amount of crystals. The crystals partially adhered to the wall surface of the reaction vessel. After crystals not adhering to the wall surface of the reaction vessel (also referred to below as a "component A") were collected, crystals adhering to the wall surface (also referred to below as a "component B") were collected separately. The collected components A and B were separately subjected to the following treatment. The collected component A or B was filtered out using a filtration device, and the compound A or B filtered out on the filtration device was showered with cyclohexane for washing. The washed component A or B was vacuum dried at 70° C. for 12 hours to yield a product including 2,6-naphthalenedicarboxylic acid dichloride. The product yielded from the component A was 15.6 g in amount, and the product yielded from the compound B was 11.1 g in amount. The total amount was 26.7 g. A percentage yield calculated from a mass yield of the compound A was taken to be a "percentage yield A", and a percentage yield calculated from a total mass yield of the compounds A and B was taken to be a percentage yield B". The percentage yield A was 53.2%, and the percentage yield B was 91.2%. Thereafter, the product yielded from the compound A and the product yielded from the compound B were mixed together for purity measurement. A purity of the mixture measured by HPLC was 98.91% by mass.

Naphthalenedicarboxylic acid dichloride of each of Comparative Examples 2 to 5 were produced by the same method as that of Comparative Example 1 in all aspects other than the following changes. Thionyl chloride and N,N-dimethylformamide were sequentially added into the three-necked flask charged with the raw material compound in Comparative Example 1. By contrast, the followings were added in Comparative Examples 2 to 5.

Comparative Example 2

In Comparative Example 2, 71.25 g of a N,N-dimethylformamide solution containing thionyl chloride (a mixed liquid of 41.25 g of thionyl chloride and 30.0 g of N,N-dimethylformamide) and 37.0 g of N,N-dimethylformamide were sequentially added into the three-necked flask charged with the raw material compound. That is, 67.0 g of N,N-dimethylformamide was used in total as a solvent and a catalyst in Comparative Example 2.

Comparative Example 3

In Comparative Example 3, 71.25 g of a 1,4-dioxane solution containing thionyl chloride (a mixed liquid of 41.25 g of thionyl chloride and 30.0 g of 1,4-dioxane), 37.0 g of 1,4-dioxane, and 4 drops (approximately 0.19 g) of N,N-dimethylformamide were sequentially added into the three-necked flask charged with the raw material compound.

Comparative Example 4

In Comparative Example 4, 71.25 g of a 1,2-dimethoxyethane solution containing thionyl chloride (a mixed liquid of 41.25 g of thionyl chloride and 30.0 g of 1,2-dimethoxyethane), 37.0 g of 1,2-dimethoxyethane, and 4 drops (approximately 0.19 g) of N,N-dimethylformamide were sequentially added into the three-necked flask charged with the raw material compound.

Comparative Example 5

In Comparative Example 5, 71.25 g of a toluene solution containing thionyl chloride (a mixed liquid of 41.25 g of thionyl chloride and 30.0 g of toluene), 37.0 g of toluene, and 4 drops (approximately 0.19 g) of N,N-dimethylformamide were sequentially added into the three-necked flask charged with the raw material compound.

Furthermore, while the reaction was caused under reflux (74° C.) in Comparative Example 1, the reaction temperature was 80° C. (non-reflux temperature) in Comparative Examples 2 to 5. Note that crystals precipitated after the reaction partially adhered to the wall surface of the reaction vessel in each of Comparative Examples 2 to 5.

Any of Examples 1 to 8 and Comparative Examples 1 to 5 having a percentage yield A of at least 80% and not causing adhesion of the resultant product to the wall surface of the reaction vessel was evaluated as being excellent in productivity. A purity of naphthalenedicarboxylic acid dichloride of at least 99.0% by mass was evaluated as high.

Table 1 below shows reaction conditions, percentage yields, purities, and occurrence or non-occurrence of adhesion to the wall surface of the reaction vessel for Examples 1 to 8 and Comparative Examples 1 to 5.

In Table 1 below, "2,6-component" and "1,4-component" under the column "Naphthalenedicarboxylic acid" represent "2,6-naphthalenedicarboxylic acid" and "1,4-naphthalenedicarboxylic acid", respectively. Also, "THF", "Dioxane", "DME", "DMF", "DEF", and "wt %" respectively represent "tetrahydrofuran", "1,4-dioxane", "1,2-dimethoxyethane", "N,N-dimethylformamide", "N,N-diethylformamide", and "% by mass". Furthermore, "–" represents non-use of a corresponding component.

TABLE 1

| | Naphthalene-dicarboxylic acid | Chlorinating agent | Solvent | Disubstituted formamide | Reaction Time [h] | Reaction Temperature | Purification method | Percentage yield [%] A | Percentage yield [%] B | Adhesion to wall surface | Purity [wt %] |
|---|---|---|---|---|---|---|---|---|---|---|---|
| Example 1 | 2,6-Component | Thionyl chloride | THF | DMF | 4 | Reflux (73° C.) | Filtration | 87.1 | | Not occurred | 99.70 |
| Example 2 | 2,6-Component | Thionyl chloride | THF | DMF | 4 | Reflux (73° C.) | Pressure reduction | 90.3 | | Not occurred | 99.42 |
| Example 3 | 1,4-Component | Thionyl chloride | THF | DMF | 4 | Reflux (73° C.) | Filtration | 86.5 | | Not occurred | 99.45 |
| Example 4 | 2,6-Component | Thionyl chloride | THF | DMF | 6 | Reflux (73° C.) | Filtration | 86.8 | | Not occurred | 99.60 |
| Example 5 | 2,6-Component | Thionyl chloride | THF | DMF | 2 | Reflux (73° C.) | Filtration | 86.5 | | Not occurred | 99.74 |
| Example 6 | 2,6-Component | Thionyl chloride | THF | DMF | 24 | 30° C. | Filtration | 88.4 | | Not occurred | 99.01 |
| Example 7 | 2,6-Component | Oxalyl chloride | THF | DMF | 4 | Reflux (73° C.) | Filtration | 88.3 | | Not occurred | 99.59 |
| Example 8 | 2,6-Component | Thionyl chloride | THF | DEF | 4 | Reflux (73° C.) | Filtration | 88.2 | | Not occurred | 99.71 |
| Comparative Example 1 | 2,6-Component | Thionyl chloride | — | DMF | 4 | Reflux (74° C.) | Filtration | 53.2 | 91.2 | Occurred | 98.91 |
| Comparative Example 2 | 2,6-Component | Thionyl chloride | — | DMF | 4 | 80° C. | Filtration | 45.5 | 90.2 | Occurred | 31.20 |
| Comparative Example 3 | 2,6-Component | Thionyl chloride | Dioxane | DMF | 4 | 80° C. | Filtration | 79.6 | 91.3 | Occurred | 98.84 |
| Comparative Example 4 | 2,6-Component | Thionyl chloride | DME | DMF | 4 | 80° C. | Filtration | 53.2 | 91.3 | Occurred | 98.84 |
| Comparative Example 5 | 2,6-Component | Thionyl chloride | Toluene | DMF | 4 | 80° C. | Filtration | 79.4 | 91.2 | Occurred | 98.56 |

The naphthalenedicarboxylic acid dichloride production method of each of Examples 1 to 8 included causing a reaction between naphthalenedicarboxylic acid and a chlorinating agent at a reaction temperature of 20° C. or higher and 75° C. or lower in the presence of a solvent including tetrahydrofuran. As a result, high-purity naphthalenedicarboxylic acid dichloride could be produced with high productivity by any of the production methods in Examples 1 to 8.

By contrast, tetrahydrofuran was not used as a solvent in the naphthalenedicarboxylic acid dichloride production method of each of Comparative Examples 1 to 5. As a result, naphthalenedicarboxylic acid dichloride produced by the production method of each of Comparative Examples 1 to 5 had insufficient purity and productivity thereof was not favorable. In particular, the production method of each of Comparative Examples 1 to 5 was determined to be unsuitable for mass production because precipitated naphthalenedicarboxylic acid dichloride partially adheres to the wall surface of a reaction vessel.

It can be determined from the above that high-purity naphthalenedicarboxylic acid dichloride can be produced with high productivity by the naphthalenedicarboxylic acid dichloride production method according to the present disclosure.

What is claimed is:

1. A naphthalenedicarboxylic acid dichloride production method comprising
    causing a reaction between naphthalenedicarboxylic acid and a chlorinating agent at a reaction temperature of 20° C. or higher and 75° C. or lower in presence of a solvent including tetrahydrofuran.

2. The naphthalenedicarboxylic acid dichloride production method according to claim 1, wherein
    the causing a reaction is performed in presence of N,N-disubstituted formamide.

3. The naphthalenedicarboxylic acid dichloride production method according to claim 2, wherein
    the N,N-disubstituted formamide is dimethyl formamide or diethyl formamide.

4. The naphthalenedicarboxylic acid dichloride production method according to claim 1, wherein
    the chlorinating agent is thionyl chloride or oxalyl chloride.

5. The naphthalenedicarboxylic acid dichloride production method according to claim 1, wherein
    the naphthalenedicarboxylic acid is 2,6-naphthalene dicarboxylic acid and naphthalenedicarboxylic acid dichloride is 2,6-naphthalenedicarboxylic acid dichloride, or
    the naphthalenedicarboxylic acid is 1,4-naphthalenedicarboxylic acid and naphthalenedicarboxylic acid dichloride is 1,4-naphthalenedicarboxylic acid dichloride.

* * * * *